US00PP09955P

United States Patent [19]

Bottoms et al.

[11] Patent Number: Plant 9,955

[45] Date of Patent: Jul. 8, 1997

[54] *SCHEFFLERA ARBORICOLA* 'PVN-1'

[75] Inventors: Ellsworth D. Bottoms; Luseane M. Bottoms, both of Apopka, Fla.

[73] Assignee: Pine Valley Nursery, Inc., Apopka, Fla.

[21] Appl. No.: 426,880

[22] Filed: Apr. 24, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 6,134 3/1988 Gorvel ..... Plt./88.1

OTHER PUBLICATIONS

Trademark for "Luseane" as recorded on Dialog file Trademark–scan file 246.

*Primary Examiner*—James R. Feyrer

*Attorney, Agent, or Firm*—Frank B. Robb; John H. Vynalek

[57] ABSTRACT

A *Schefflera arboricola* which truly a dwarf cultivar wherein the various dimensions of the plant parts are proportionally smaller, but is of substantially the same color as the usual plant, the instant plant having been asexually reproduced from a bud sport initially discovered on a normal sized *Schefflera arboricola*.

1 Drawing Sheet

BACKGROUND OF THE INVENTION

This invention relates to a new and distinct cultivar of *Schefflera arboricola* named 'PVN-1'.

This cultivar is in fact a dwarf wherein all of the usual elements of the known, standard *S. arboricola* are present but on a dwarf scale, including color, shape of leaves, shape of plant and all other parts of similar size.

The cultivar was discovered as a sport of a standard *S. arboricola* grown in a nursery in Apopka, Fla., where we are growing other *S. arboricola,* and was noticed because of its small size, being carefully removed from the parent and thereafter used for initial propagation. The 'PVN-1' is part of a continuing effort to develop plants of this species. Another *S. arboricola,* which herein is designated as 'Luseane' (unpatented) is also a dwarf and a sport from a standard *S. arboricola.* The 'PVN-1' is a subsequent sport and differs significantly from the 'Luseane' as shall be described herein. It is contemplated, though, that notwithstanding the distinction between the 'PVN-1' and the 'Luseane', 'PVN-1' shall be marketed under the same commercial name "Luseane". Marketing of the earlier plant 'Luseane' has been discontinued for some time.

We have initially effected asexual propagation by stem cuttings in Apopka, Fla., as well as by tissue culture. We have observed the plants thus produced and find that the characteristics initially described are in fact reproduced in successive generations.

We believe the plant provides an attractive commercial plant of small an unusual size for many decorative purposes.

SUMMARY OF THE INVENTION

The 'PVN-1' has very short internodes and small leaves. The petiole length is also much shorter than the standard *S. arboricola.* Specifically, the plant of this application is a dwarf of the standard *S. arboricola.* This is reflected in leaflet and compound leaf size, as well as, internode and petiole length.

The 'Luseane', although also a dwarf of the standard *S. arboricola,* is a thinner, generally weaker, plant, both in actuality and appearance. The 'PVN-1' generally produces seven (7) to eight (8) leaflets for each compound leaf while the 'Luseane' generally produces six (6) leaflets for each compound leaf. In addition, the PVN-1 is much denser and stronger than the 'Luseane' due to the shorter internode and petiole lengths. This presents a plant that is, not only desirable for its appearance, but also for its structural superiority from that of the 'Luseane'.

When the foregoing are present in a single specimen, these differences from a standard *S. arboricola* and the 'Luseane', create a dramatically different cultivar of very attractive appearance which distinguish it from the *S. arboricola* and 'Luseane'.

While the traditional *S. arboricola,* which is grown as an indoor foliage plant, attains a size which occupies substantial space, the plant hereof is more of a pot plant for use in decorative combinations and is more nearly a small plant for use with other plants which desirably have more outstanding colors.

In carrying out cultivation of specimens which have been asexually reproduced, we have found that the cultivar herein identified as PVN-1 when grown in a group of five three-quarter inch cuttings under appropriate condtions will reach a mature size of 40 to 60 cm in width and 40 to 50 cm in height over a period of six months.

DESCRIPTION OF THE DRAWINGS

This new variety of *S. arboricola* is illustrated by the accompanying photographic drawings which depict the plant by the best possible color representation using color photography and compare it to the 'Luseane'.

The first drawing herewith discloses a typical plant and shows the same in as nearly true color as photography will provide, having the shape and size with the dimensions previously stated.

The second drawing compares the 'PVN-1' (left) with the 'Luseane' (right) which were from the same growing area and grown under identical conditions.

BOTANICAL DESCRIPTION OF THE PLANT

In describing the color set forth below, The Royal Horticultural Society (R.H.S.) Colour Chart is referred to for comparison.

To further define the aspects of the cultivar here being described, a summary of many of the dimensions is set out below:

Leaves: The largest leaflets of a mature sized specimen are approximately 4.0–4.5 cm in length, and 1.5–2.0 cm in width. The compound leaf on a mature specimen is 7–10 cm at its widest part. The top surface of the leaflets are glossy with the color for a mature leaflet being: top surface-R.H.S. 139A; bottom surface-R.H.S. 146A/B.

Petiole: The petiole is approximately 5.5–7.5 cm in length. The color of the petiole is R.H.S. 144A.

Internode: The internode averages about 0.9–1.1 cm in length.

Stem: Stem color is R.H.S. 144A.

A comparison of the standard *S. arboricola,* 'Luseane', and 'PVN-1' is shown in the following table:

| Measurements | *S. arboricola* | 'Luseane' | 'PVN-1' |
|---|---|---|---|
| Leaflet Length: | 7.0–10.0 cm | 6.0–8.0 cm | 4.0–4.5 cm |
| Leaflet Width: | 2.0–4.0 cm | 1.5–2.5 cm | 1.5–2.0 cm |
| Petiole Length: | 10.0–15.0 cm | 7.0–9.0 cm | 5.5–7.5 cm |
| Internode Length: | 2.0–3.0 cm | 1.1–1.3 cm | 0.9–1.1 cm |

The leaflet, petiole and stem colors appear to be substantially the same as the normal size *S. arboricola.*

We claim:

1. A dwarf *Schefflera arboricola* plant, substantially as herein shown and described, characterized particularly as to novelty by its almost perfectly dwarfed dimensions as compared with the usual *Schefflera arboricola.*

* * * * *

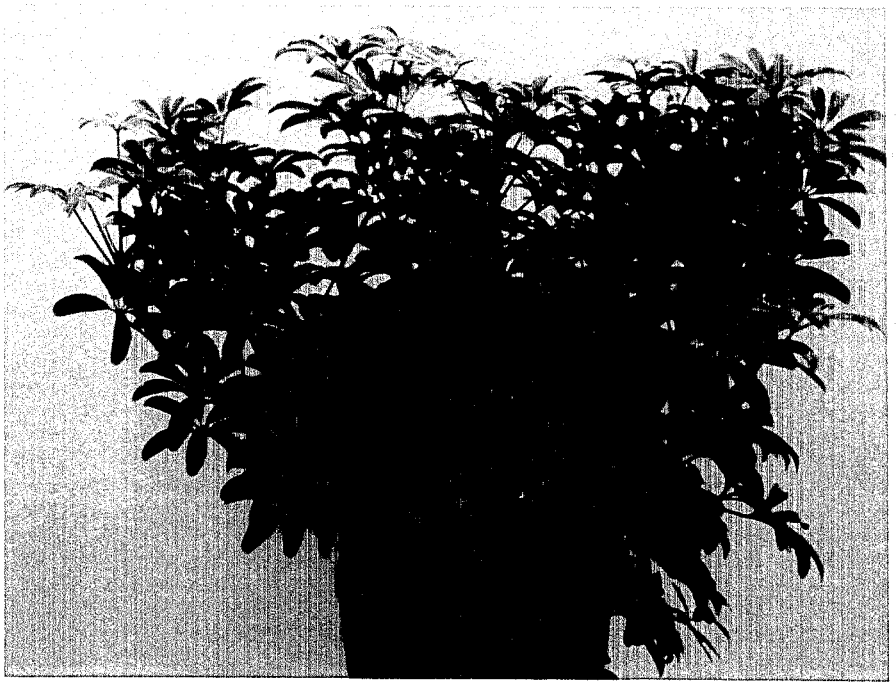
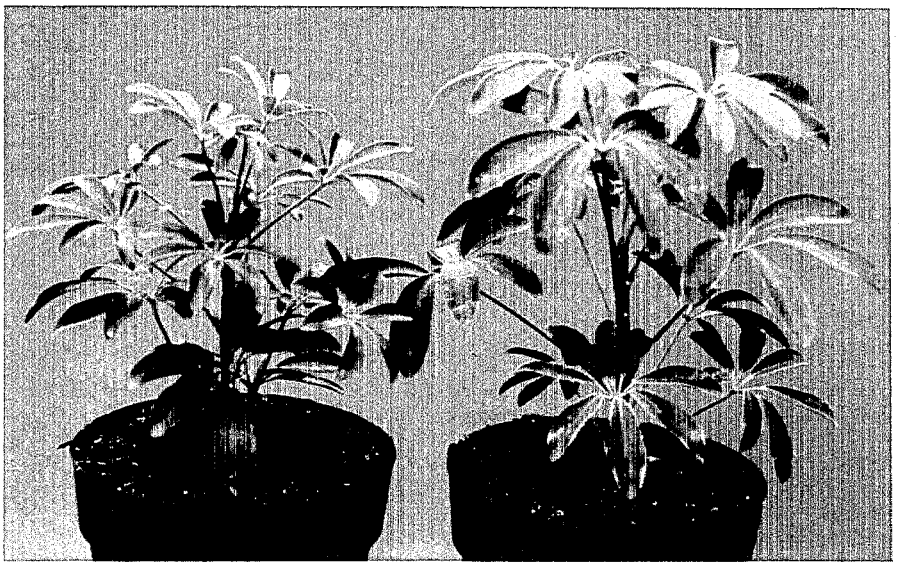
'PVN-1' 'LUSEANE'